(12) United States Patent
Larsson

(10) Patent No.: US 7,976,533 B2
(45) Date of Patent: Jul. 12, 2011

(54) DRAINAGE APPARATUS AND METHOD

(75) Inventor: Michael Larsson, Zug (CH)

(73) Assignee: Medela Holding AG, Baar (CH)

( * ) Notice: Subject to any disclaimer, the term of this patent is extended or adjusted under 35 U.S.C. 154(b) by 710 days.

(21) Appl. No.: 10/579,982

(22) PCT Filed: Dec. 22, 2003

(86) PCT No.: PCT/CH03/00841
§ 371 (c)(1),
(2), (4) Date: May 19, 2006

(87) PCT Pub. No.: WO2005/061025
PCT Pub. Date: Jul. 7, 2005

(65) Prior Publication Data
US 2007/0078444 A1    Apr. 5, 2007

(51) Int. Cl.
*A61M 1/00* (2006.01)

(52) U.S. Cl. ........ 604/540; 604/104; 604/174; 604/256; 604/250; 604/247; 604/239; 604/329; 604/542; 604/544; 600/29; 600/30; 600/31

(58) Field of Classification Search .................. 604/540, 604/542, 544
See application file for complete search history.

(56) References Cited

U.S. PATENT DOCUMENTS

| | | | |
|---|---|---|---|
| 4,342,315 A * | 8/1982 | Jackson | 604/35 |
| 4,536,180 A | 8/1985 | Johnson | |
| 4,735,606 A | 4/1988 | Davison | |
| 5,112,302 A * | 5/1992 | Cucin | 604/35 |
| 5,738,656 A | 4/1998 | Wagner | |
| 6,129,701 A | 10/2000 | Cimino | |
| 7,025,718 B2 * | 4/2006 | Williams | 600/18 |

* cited by examiner

*Primary Examiner* — Michele Kidwell
*Assistant Examiner* — Ilya Y Treyger
(74) *Attorney, Agent, or Firm* — McDonnell Boehnen Hulbert & Berghoff LLP

(57) ABSTRACT

An apparatus for removing body fluids from a body cavity by suction, such as a thorax, gastric or any other human body cavity or a wound, comprises means (9) to increase the pressure difference between a pressure in a drainage lumen (3) and a pressure in the atmosphere when an auxiliary lumen (5) is open. The apparatus enables removal of clots or other plugs of the catheter and drainage tube in an efficient and not patient disturbing way.

4 Claims, 2 Drawing Sheets

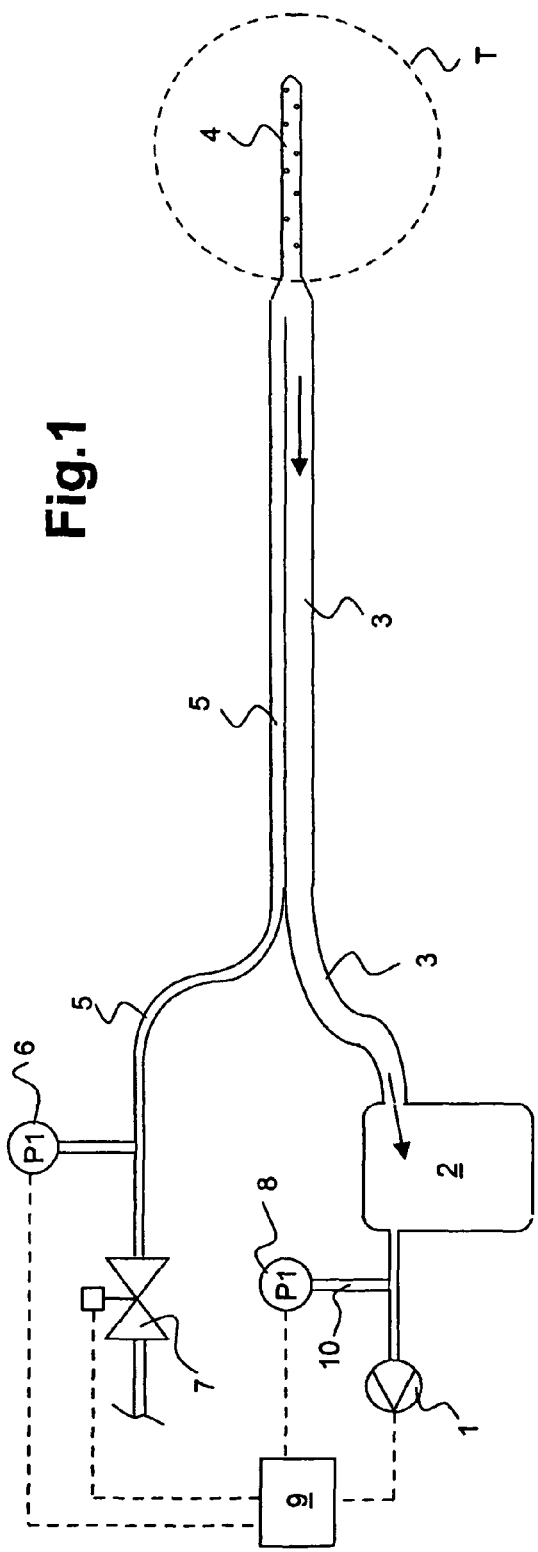
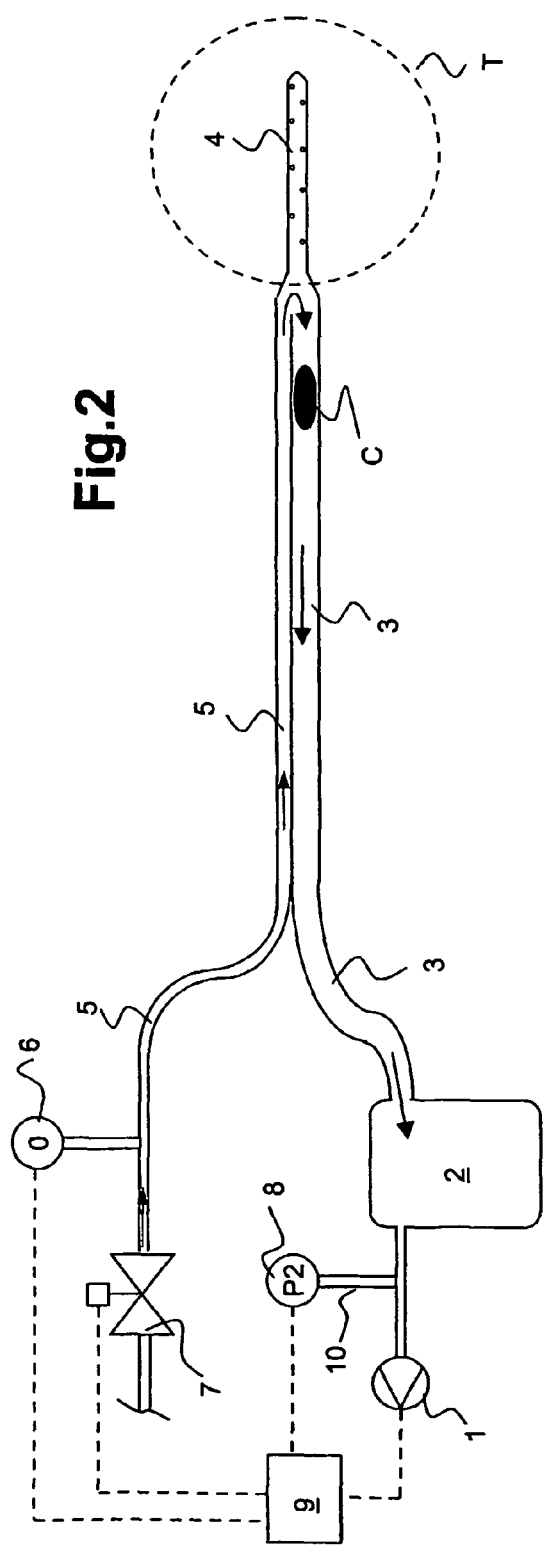

DRAINAGE APPARATUS AND METHOD

TECHNICAL FIELD

This invention relates to a drainage apparatus and a method for removing fluids from a body cavity, preferably a chest drainage apparatus.

BACKGROUND OF THE INVENTION

A drainage apparatus is used for draining fluid from a human body cavity or wound to promote healing, such as after chest surgery. The apparatus usually comprises a suction pump, a collection container which is often connected with an underwater seal container, and a drainage tube having a distal and a proximal end. The proximal end of this tube is connected to a catheter which is introduced in the body cavity, the distal end extends into the collection container or the underwater seal container respectively. The negative pressure applied has to be chosen carefully, since excessive pressure may damage delicate tissues in the body cavity.

Blood or tissue clots however can clog the catheter or the drainage tube, such that the fluids can no longer readily drain into the fluid collection container but tend to built up in the catheter, the drain tube or may even remain in the cavity. It is therefore necessary to sometimes vent the body cavity to remove drainage fluids.

It is known to use an auxiliary line whose proximal end is in fluid contact with the drainage line. This auxiliary line is used to supply air or a gas to the drainage line.

The supply is controlled by a valve and a pressure sensor. Such an apparatus is for example described in U.S. Pat. No. 5,738,656.

However, the catheter and the drainage tube have still to be removed and cleaned, when they are clogged.

SUMMARY OF THE INVENTION

It is an object of the invention to provide a method and an apparatus for removing fluids from a body cavity which enables removal of clots in the catheter and the drainage tube in a more simple and more expedient way.

This object is achieved by an apparatus and a method with the features according to claims 1 and 4.

The inventive apparatus for removing body fluids from a body cavity by suction, such as a thorax, gastric or any other human body cavity or from a wound, comprises the same basic elements as the apparatus known in the prior art. However, means are provided to increase the pressure difference between a pressure in a drainage lumen and a pressure in the atmosphere when an auxiliary lumen is open. In a preferred embodiment, this means is a control which controls a suction pump and which therefore increases the suction power of the suction pump.

Since the auxiliary lumen is open and air from the atmosphere or a gas can be introduced to the body cavity, the pressure in this cavity will be equal or at least near to atmospheric pressure or even to a higher pressure applied by the auxiliary lumen. However, by increasing the pressure in the drainage lumen at the distal end of the drainage lumen, the clot in the drainage lumen or the catheter can be removed through this distal end without any risk that any damages in the cavity may occur. When the clot is finally removed, the pressure in the system is equal or near the atmospheric pressure, since the auxiliary lumen is still open. No damage to the body cavity can occur at this stage either.

Clots can therefore easily be removed, without having to disturb the patient by removing and reentering the drainage tube.

Additional features of the present invention having additional advantages are described in the dependent claims.

BRIEF DESCRIPTION OF THE DRAWING

The invention is explained hereinbelow in more detail and will become more apparent from the accompanying drawing.

FIG. 1 shows a schematic view of the inventive apparatus during drainage;

FIG. 2 shows the apparatus during removal of a secret clot and

DETAILED DESCRIPTION OF THE PREFERRED EMBODIMENT

Figure 3:
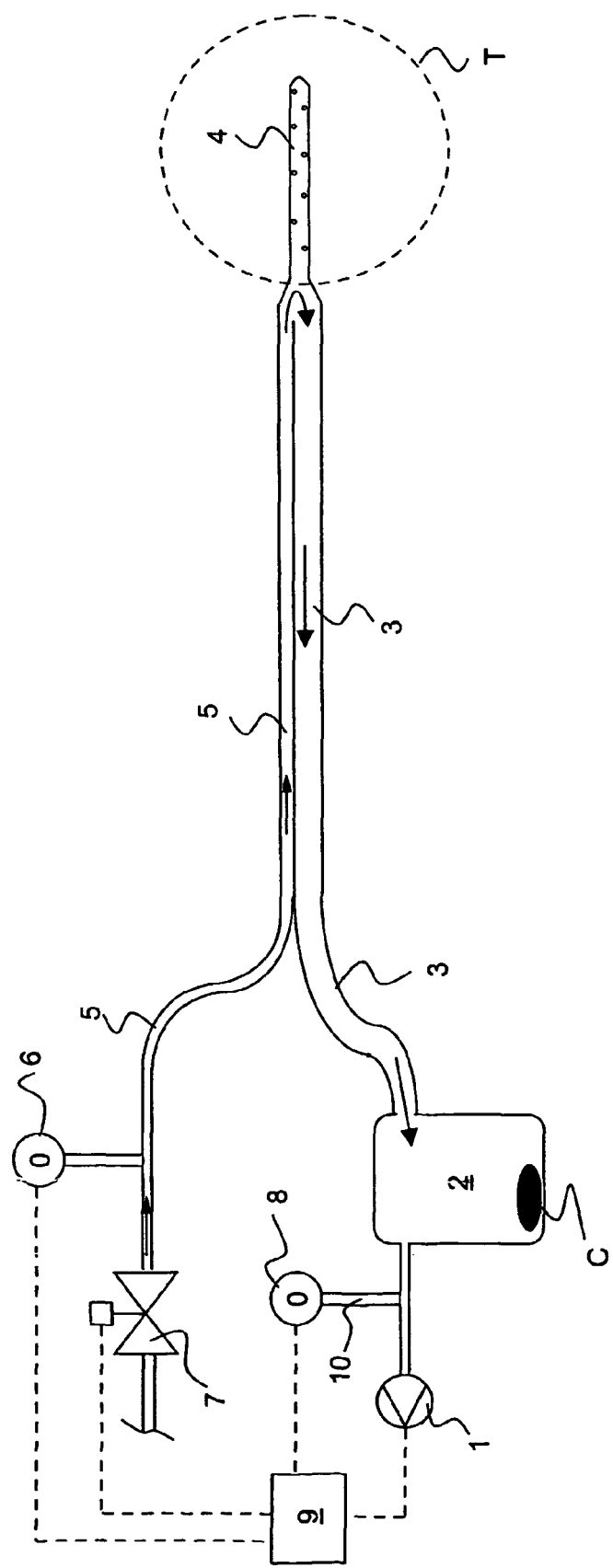
FIG. 3 shows the apparatus after removal of the clot.

The apparatus according to the invention comprises a suction source, preferably a suction pump 1; suction drainage collection means comprising a drainage fluid collection container 2 or comprising a container system having in addition an underwater seal container; a catheter means comprising a drainage lumen 3, a catheter 4 and an auxiliary lumen 5; a first pressure sensor 6; a valve 7; a second pressure sensor 8 and a controller 9.

The suction pump 1 is connected to the drainage fluid collection container 2 by a tube 10. The second pressure sensor 8 measures the pressure in this tube 10. The second pressure sensor 8 can also be placed in the fluid collection container 2 or the drainage lumen 3. The drainage fluid collection container 2 is closed by an airtight lid. So is the underwater seal, when one is used. The drainage lumen 3 comprises a distal end, which is connected to an opening of the container 2. The proximal end of the drainage lumen 3 ends in the catheter 4 adapted for placement adjacent a wound in a body cavity T, for example a chest. The proximal end of the drainage lumen 3 is also in fluid communication with a proximal end of the auxiliary lumen 5. Preferably, the two lumens 3,5 are formed by a double lumen tube which is divided at the distal end in two separate tubes, each one forming a distal end of the auxiliary tube 5 and the drainage tube 3 respectively. However, they can also be two separate tubes.

The region of the distal end of the auxiliary lumen 5 is provided with the first pressure sensor 6 and can be closed by means of a valve 7.

A controller 9 is in communication with at least the section pump 1 and one of the group of the first pressure sensor 6, the second pressure sensor 8 and the valve 7. Preferably, the controller 9 is in communication with all of these elements.

The suction pump 1 is a suction pump known in the art, wherein the power of the pump 1 and therefore the generated negative pressure can be varied by use of the controller 9. The valve 7 is a valve known in the art and can preferably be controlled electronically by use of the controller 9. The first and second pressure sensors 7, 8 are sensors known in the art and can preferably be read by the controller or can send their measured data to the controller. The connections between these elements and the controller is preferably wired, however, wireless communication or data transfer is possible too.

FIG. 1 shows the use of the apparatus during normal drainage. The suction pump 1 generates a negative pressure $P_1$, normally about −30 cmH$_2$O (≈3 kPa). The valve 7 is closed. This causes the body fluid to be sucked from the cavity T through the drainage lumen 3 into the fluid collection container 2. An arrow shows the direction of this flow. The first and second pressure sensors 7, 8 measure the same pressure $P_1$. When a clot C is sucked from the cavity T into the drainage lumen 3, it can easily be removed during a venting cycle as can be seen in FIG. 2. The valve 7 is opened which causes the pressure in the auxiliary lumen 5 to increase at least to atmospheric pressure since by opening the valve 7 fresh air is supplied to the auxiliary lumen 5. It is also possible increase the pressure even more by pumping air or a gas through the valve 7 into the auxiliary lumen 5. The air flow is also marked with an arrow. When the valve is open or at the same time as opening the valve, the suction power of the suction pump 1 is increased. This increases the pressure difference between the pressure in the drainage lumen 3 and the atmosphere. Preferably, the pressure difference can be increased to achieve a negative pressure level in the drainage lumen 3 which is at least half of the negative pressure level during normal drainage. This increase will suck the clot C in direction to the container 2. The pressure measured with the first pressure sensor 6 is 0 cmH$_2$O or a positive pressure higher than atmospheric pressure, the pressure measured with the second pressure sensor 8 is $P_2$. $P_2$ can for example be −650 cmH$_2$ (≈64 kPa).

In FIG. 3 the clot C has arrived at the container 2 and the drainage lumen 3 is open.

Both pressure sensors 7, 8 measure 0 cmH$_2$O. The valve 7 can be closed again and the normal drainage cycle can restart.

If the controller 9 is coupled to the first pressure sensor 6, pressure changes caused by clots C being sucked into the drainage lumen 3 can be detected. This can be used as a signal for the controller 9 to automatically open the valve 7 of the auxiliary lumen and to automatically increase the suction power and therefore the pressure difference. The second pressure sensor 8 can indicate the controller 9, that the clot C has been removed and that the drainage lumen 3 is open again. The controller 9 can then automatically decrease the suction power to normal drainage power and can afterwards close the valve 7 in order to start the normal drainage process. However, it is also possible to operate the controller manually and to separately open and close the valve. In a simple embodiment, the controller is a knob for changing the suction power of the suction pump 1.

The pressure difference can be increased continuously or abruptly by either increasing the suction power smoothly or abruptly. Which procedure leads to better results depends on the kind of cavity and the kind of fluid to be sucked. In order to prevent any damages to the patient, the pressure difference is increased only when the pressure corresponds at least to atmospheric pressure.

The inventive apparatus and method enable removal of clots or other plugs of the catheter and drainage tube in an efficient and not patient disturbing way.

LIST OF REFERENCE NUMBERS

T body cavity.
C Clot
1 suction pump
10 tube
2 drainage fluid collection container
3 drainage lumen
4 catheter
5 auxiliary lumen
6 frist pressure sensor
7 valve
8 second pressure sensor
9 controller

The invention claimed is:

1. A method for operating an apparatus for removing body fluids from a body cavity by suction, the apparatus comprising:
   a catheter having a drainage lumen and an auxiliary lumen adapted for placement adjacent a wound in the body cavity to be drained of body fluid, the drainage lumen having a proximal end being in fluid communication with a proximal end of the auxiliary lumen;
   a container for connection in fluid communication with the drainage lumen and for receiving body drainage fluid from the body cavity;
   a source of suction for effecting negative pressure in the drainage lumen and a valve for opening the auxiliary lumen in order to supply air or gas to the body cavity;
   the method comprising the steps of
   measuring the pressure in the auxiliary lumen,
   opening the auxiliary lumen; and
   increasing the pressure difference between a pressure in the drainage lumen and a pressure in the atmosphere only when the pressure measured in the auxiliary lumen corresponds at least to atmospheric pressure, wherein the pressure difference is increased by increasing the power of the source of suction.

2. The method of claim 1 wherein the auxiliary lumen is opened by opening a first valve.

3. The method of claim 2 wherein the source of suction is controlled by a controller and wherein the controller is in communication with at least one of the group of the valve and a first pressure sensor measuring the pressure in the auxiliary lumen.

4. A method for removing body fluids from a body cavity by suction, the method comprising the steps of:
   providing a catheter having a drainage lumen and an auxiliary lumen adapted for placement adjacent a wound in the body cavity to be drained of body fluid, the drainage lumen having a proximal end being in fluid communication with a proximal end of the auxiliary lumen;
   providing a container for connection in fluid communication with the drainage lumen and for receiving body drainage fluid from the body cavity;
   providing a source of suction for effecting negative pressure in the drainage lumen and
   providing a valve for opening the auxiliary lumen in order to supply air or gas to the body cavity
   the method further comprising the steps of
   measuring the pressure in the auxiliary lumen,
   opening the auxiliary lumen; and
   increasing the pressure difference between a pressure in the drainage lumen and a pressure in the atmosphere only when the pressure measured in the auxiliary lumen corresponds at least to atmospheric pressure, wherein the pressure difference is increased by increasing the power of the source of suction.

* * * * *